United States Patent [19]

Valk

[11] Patent Number: 4,567,671

[45] Date of Patent: Feb. 4, 1986

[54] METHOD FOR ASSESSING THE BODY LENGTH, METHOD OF ASSESSING A GROWTH CURVE AND DEVICE FOR CARRYING OUT SUCH MEASUREMENTS

[76] Inventor: Ignatius M. Valk, Dasstraat 2, 6531 TA Nijmegan, Netherlands

[21] Appl. No.: 503,213

[22] Filed: Jun. 10, 1983

[30] Foreign Application Priority Data

Jun. 16, 1982 [NL] Netherlands .................. 8202443

[51] Int. Cl.[4] ............................................. G01B 7/02
[52] U.S. Cl. .................................. 33/512; 33/169 R
[58] Field of Search ............ 33/174 D, 174 R, 169 R, 33/143 R, 143 M, 143 L, 511, 512, 515; 128/781

[56] References Cited

U.S. PATENT DOCUMENTS 3,196,551 7/1965 Provost et al. .
3,575,159 4/1971 Pile .
4,062,605 12/1977 Peters .

FOREIGN PATENT DOCUMENTS 174443 9/1906 Fed. Rep. of Germany .
1541118 5/1969 Fed. Rep. of Germany .
436546 1/1912 France .

OTHER PUBLICATIONS

Selvik, Proc. Soc. Photo-Optical Inst. Engineers, vol. 166, 7/78, pp. 184–191.

Primary Examiner—Harry N. Haroian
Attorney, Agent, or Firm—Thomas S. MacDonald; Alan H. MacPherson; Steven F. Caserza

[57] ABSTRACT

A method of assessing the body length by carrying out a length measurement, in which the length of the lower leg is measured and the measured leg is multiplied by a person-bound factor. A device for carrying out the measurement comprises a chair part a and a measuring part b, at least one of the parts a and b being adjustable in a direction of height and displaceable in a forward (backward) direction, said measuring part comprising one or two posts along which at least one measuring plate can be placed on the knee.

12 Claims, 1 Drawing Figure

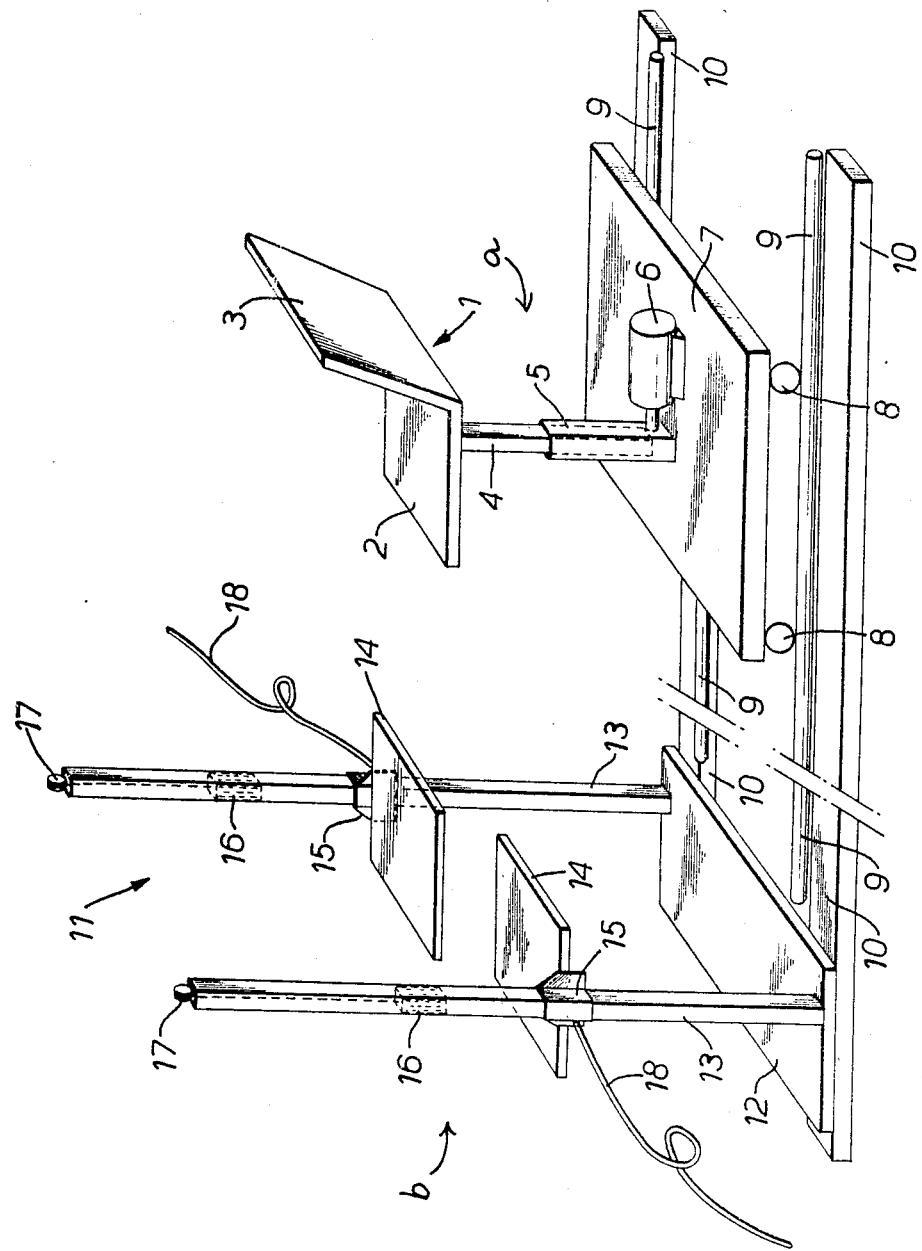

METHOD FOR ASSESSING THE BODY LENGTH, METHOD OF ASSESSING A GROWTH CURVE AND DEVICE FOR CARRYING OUT SUCH MEASUREMENTS

The invention relates to a method of assessing the body length by carrying out a length measurement. The invention furthermore relates to a method of assessing a growth curve and to a device for carrying out such a measurement.

It is generally known that measuring the body length is a measurement frequently carried out, though, as is known, with poorly reproducible results and with a high rate of deviation, so that for obtaining medical data such measurements are hardly reliable. On the basis of such body length measurements only a little reliable growth curve can be composed. Yet the assessment of a reliable growth curve is of high importance, for example, for measuring the influence of certain medical preparations on the physical growth and, for example, for assessing when the growth rate is at a maximum.

In order to obtain a more reliable measurement of the growth curve Selvic has developed a method in which metal pellets were introduced into bones of the persons to be measured and subsequently the growth curve was assessed by means of X-ray photographs, on which the distance between the pellets was measured. This method described by Aronson (1976) "X-ray Stereophotogrammetry of longitudinal bone growth" in AV-Centralen provided, indeed, a reasonably reliable growth curve, but this method can be carried out only with difficulty and making a large number of X-ray photographs has certain disadvantages. Moreover, this method can only be carried out by specialists. Valk has developed a method of assessing the body length by measuring the length of the fore-arm (see Valk Thesis 1974 and Thesis of van den Bosch 1981). A fixed correlation was found between the length of the fore-arm and the body length so that the growth curve of the fore-arm could be used as a growth curve for the body. This method, which has been employed for more than ten years already, provided a considerable improvement over the Selvic method, but it has now been found possible to improve the Valk method to an extent such that the standard deviation of the measurement can be improved by more than a factor 2. The method now invented is characterized in that the length of the lower leg is measured and the length found is multiplied by a given factor for assessing the body length. In particular, the distance between the underside of the foot and the top side of a bent knee is measured. In this way a very accurate growth curve can be measured by carrying out in known manner a plurality of measurements in the course of time, the measuring data being plotted in a graph for which a very accurate measurement of length can now be used as described above. The factor is person-bound.

For carrying out such a method there has now been developed a device, which will be described more fully hereinafter with reference to the accompanying drawing. This device permits of carrying out a very accurate measurement with a mean standard deviation of measuring error of $SD = \pm 0.09$ mm.

The device according to the invention comprises two interconnected parts i.e. a chair a and a measuring part b.

The presented FIGURE is a partial perspective view of the apparatus of the invention.

The chair part comprises a chair 1 having a seat 2, a back 3, a leg 5 and a shaft 4 slidable in said leg 5. The height of the chair may be adjustable with the aid of setting members 6. This chair is placed on a platform 7, which is displaceable by ball bearings 8 on a rail 9 arranged on a beam 10. By means of the beam 10 the chair part is connected with the measuring part. The measuring part preferably comprises two posts 13, placed on the foot support 12, arranged on the beams 10. Along the posts 13, measuring plates 14 are slidable with the aid of clamps 15. In order to compensate the weight of the measuring plates 14 for a major part they are connected with a counter-weight 16, which is connected through a pulley 17 with the measuring plate 14. A lead 18 is connected with the clamp 15 to enable electronic reading, if desired.

The device for carrying out the measurement essentially comprises a chair part a and a measuring part b, at least one of the parts a or b being adjustable in a direction of height and displaceable in forward (rearward) direction, said measuring part comprising one or two beams along which at least one measuring plate can be placed on the knee. Although it is preferred to have the chair adjustable in a direction of height and displaceable in a forward and backward direction, the foot support and the measuring face may, as an alternative, be adjustable in a direction of height whilst the measuring part is shifted in a forward and rearward direction. Measurements carried out in practice have shown that it is important for the person concerned to be influenced at a minimum by the measurement being carried out, which can be ensured by moving the chair in a vertical and a horizontal direction.

The measuring part 11 comprises a foot support and a measuring plate, which is adjustable in a direction of height. In the practical measurement the distance between the support and the measuring plate is determinative and this distance can be read in various ways, which reading should be accurate to 0.1 mm. Preferably the measuring part comprises two posts and two measuring faces so that the length of the two lower legs can be simultaneously measured.

A measurement in accordance with the invention can be carried out as follows. The person whose growth curve has to be assessed sits down on the chair 1, the height of which is adjusted so that the person's foot bears on the foot support 12, whilst the chair is moved into a position such that the lower leg is at an acute angle to the upper leg. A given person is placed in a reproducible manner on the chair, whilst the height of the chair and the distance between the chair and the measuring part are adjusted with an accuracy of about 1 mm. A deviation of the chair setting of about 1 cm results in a measuring error of about 0.2 mm. Then the measuring plate 14 is arranged on the upper leg and the chair part is moved in forward direction along the frame (9,10) so that an acute angle is formed between the upper leg and the lower leg, whilst the measuring plate will first be moved upwards and will subsequently be lowered. The maximum distance between the foot support and the measuring face is considered to be assessed when for the topmost point and directly after the topmost point a distance is found which is 0.1 mm smaller. As soon as this maximum distance is found, a check is carried out by moving the knee in a direction at right angles to the first direction so that by moving the knee over a distance of a few centimeters a difference in distance has to be found of 0.1 mm below the first topmost point. If this difference were more than 0.1 mm, it is advisable to repeat the measurement because in this case the muscular stress has brought about a non-optimum measurement.

Recapitulating it can be said that it is now possible to assess a very accurate growth curve of persons.

The figures used in the claims are only meant to explain more clearly the intention of the invention and are not supposed to be any restriction concerning the interpretation of the invention.

I claim:

1. A method of assessing human body length of a given person by carrying out a length measurement comprising sitting a given person so that the lower leg of that person is at an angle to the upper leg; measuring the length of the lower leg and multiplying the measured length of said lower leg by a factor which is a previously measured ratio of the given person's total body length to the given person's lower leg length, said method being carried out by a device comprising means for sitting a person in a position so that the person's knee is bent and measuring means for measuring the length of the leg from the top of the knee, at least one of said means being adjustable in a direction of height and displaceable in a forward or backward direction, said measuring means comprising one or two posts along which at least one measuring plate can be placed on the knee.

2. A device as claimed in claim 1 wherein said first means is a chair and both of said means together forming a single unit, both of said means being arranged on a frame.

3. A device as claimed in claims 1 or 2 wherein said sitting means is adjustable in a direction of height and slidable along a frame in a forward and a backward direction.

4. A device as claimed in claims 1, 2 or 3 wherein the measuring means comprises a foot support on a frame, two posts connected to and extending above said support, a measuring plate slidably mounted on said posts and means for indicating the height of said plate with respect to said frame.

5. A device as claimed in claim 4 wherein said plate is connected through a pulley with a counter-weight.

6. A method of assessing human body length of a given person by carrying out a length measurement comprising sitting a given person to that the lower leg of that person is at an angle to the upper leg; measuring the length of the lower leg and multiplying the measured length of said lower leg by a factor which is a previously measured ratio of the given person's total body length to the given person's lower leg length and wherein said person is placed on a chair, adjusting the height of the chair so that the person's feet are flatly bearing on a foot support and adjusting the location of said chair relative to a measuring plate so that an acute angle is formed between the lower leg and the upper leg, bringing said measuring plate into contact with the upper leg, moving said chair until a more acute angle is formed between the upper leg and the lower leg, during which movement the maximum distance between the foot support and the measuring plate is measured.

7. A method as claimed in claim 6 wherein by way of a check, moving the upper leg over a distance of a few centimeters in a direction at right angles to said last chair movement, the influence of said right angle movement on the distance between the foot support and the measuring plate being assessed.

8. A method of assessing human body length of a given person by carrying out a length measurement comprising sitting a given person so that the lower leg of that person is at an angle to the upper leg; measuring the length of the lower leg and multiplying the measured length of said lower leg by a factor which is a previously measured ratio of the given person's total body length to the given person's lower leg length, wherein the measuring is performed by measuring the distance between the underside of a foot and the top side of a bent knee, and wherein said person is placed on a chair, adjusting the height of the chair so that the person's feet are flatly bearing on a foot support and adjusting the location of said chair relative to a measuring plate so that an acute angle is formed between the lower leg and the upper leg, bringing said measuring plate into contact with the upper leg, moving said chair until a more acute angle is formed between the upper leg and the lower leg, during which movement the maximum distance between the foot support and the measuring is measured.

9. A device for measuring the length of the lower leg of a human body comprising:
   first means for sitting a person so that its lower leg is at an acute angle to its upper leg;
   second means for measuring the length of said lower leg from the top of the knee to the bottom of the foot; and
   means for adjusting the distance between said first means and second means to vary said acute angle and assure measurement of the maximum distance between said top of the knee and said bottom of the foot.

10. The device as set forth in claim 9 in which said first means comprising a slidable chair.

11. The device as set forth in claim 9 in which said second means comprises a horizontal foot support, a vertically slidable measuring plate adapted to rest on the top of the knee and means for measuring the distance between said support and said plate.

12. The device as set forth in claim 11 in which said first means is a vertically adjustable and horizontally slidable chair.

* * * * *